US00PP33408P3

(12) United States Plant Patent
Juneau

(10) Patent No.: US PP33,408 P3
(45) Date of Patent: Aug. 31, 2021

(54) GRAPE PLANT NAMED 'JUNEAUDOR PRÉCOCE'

(50) Latin Name: ***Vitis* hybrid**
Varietal Denomination: Juneaudor précoce

(71) Applicant: Ronald Juneau, Pont-Rouge (CA)

(72) Inventor: Ronald Juneau, Pont-Rouge (CA)

( * ) Notice: Subject to any disclaimer, the term of this patent is extended or adjusted under 35 U.S.C. 154(b) by 0 days.

(21) Appl. No.: 16/873,714

(22) Filed: Jun. 10, 2020

(65) Prior Publication Data

US 2020/0396880 P1 Dec. 17, 2020

(30) Foreign Application Priority Data

Jun. 11, 2019 (CA) ..... PBR 19-9941

(51) Int. Cl.
*A01H 5/12* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
CPC ..... A01H 6/88
See application file for complete search history.

*Primary Examiner* — Anne Marie Grunberg
(74) *Attorney, Agent, or Firm* — Penny J Aguirre

(57) ABSTRACT

The invention is a new and distinct variety of Grape plant named 'Juneaudor précoce' that is characterized by its grape clusters with shoulders that are loose in density, its very early fruit maturity period, its vigorous growth habit with high fruit productivity, its good fruit set, its grapes that have thick skins, and its grapes that produce wine that is rich in aroma, juicy, vinous with a fruity taste.

3 Drawing Sheets

Botanical classification: *Vitis* hybrid.
Variety denomination: 'Juneaudor précoce'.

CROSS-REFERENCE TO A RELATED APPLICATION

This application claims priority to a Canadian plant breeders' rights application filed on Jun. 11, 2019, application No. 19-9941, under 35 U.S.C. 119(f), the entire contents of which is incorporated by reference herein.

BACKGROUND OF THE INVENTION

The present invention relates to a new and distinct cultivar of grape plant botanically of hybrid origin and known as *Vitis* 'Juneaudor précoce', referred to hereafter by its cultivar name, 'Juneaudor précoce'.

The new cultivar was derived from a controlled breeding program conducted by the Inventor in Portneuf County, Québec, Canada. The objective of the breeding program is to develop new cold hardy grape varieties with reliable winter hardiness in Québec combined with good winemaking characteristics.

The new cultivar arose from open pollination in 2002 of an unnamed and unpatented proprietary plant in the Inventor's breeding program, reference no. "27 Auger" as the female parent. The male parent is therefore unknown. The new *Vitis* was selected as a single unique plant in 2016 from the resulting seedlings.

Asexual propagation of the new cultivar was first accomplished by hardwood stem cuttings in 2012 by the Inventor in St-Ubalde, Québec, Canada. Asexual propagation of the new cultivar by hardwood stem cuttings has determined that the characteristics are stable and true to type in successive generations.

SUMMARY OF THE INVENTION

The following traits have been repeatedly observed and represent the characteristics of the new cultivar. These attributes in combination distinguish 'Juneaudor précoce' as a new and unique cultivar of *Vitis*.

1. 'Juneaudor précoce' exhibits grape clusters with shoulders that are loose in density.
2. 'Juneaudor précoce' exhibits a very early fruit maturity period; 3 weeks before the grape varities grown under the same conditions by the Inventor.
3. 'Juneaudor précoce' exhibits a vigorous growth habit with high fruit productivity.
4. 'Juneaudor précoce' exhibits grapes that are gold in color at full maturity.
5. 'Juneaudor précoce' exhibits good fruit set.
6. 'Juneaudor précoce' exhibits grapes that have thick skins.
7. 'Juneaudor précoce' exhibits grapes that produce wine that is rich in aroma, juicy, vinous with a fruity taste.

The female parent plant of 'Juneaudor précoce' differs from 'Juneaudor précoce' in having leaves that are different in form and appearance, grape clusters that are different in shape and fruits that are different in color and size and mature later. 'Juneaudor précoce' can also be compared to the *Vitis* cultivars 'Adalmiina' (not patented) and 'Louise Swenson' (not patented). 'Adalmiina' and 'Louise Swenson' are both similar to 'Juneaudor précoce' in having fruit that is gold in color at maturity and similar berries and grape cluster characteristics. 'Adalmiina' and 'Louise Swenson' both differ from 'Juneaudor précoce' in having leaves that are different in appearance and form, berry maturity date that is much later, and much less cold hardiness, different berry flavor and different vine buds and young shoots.

BRIEF DESCRIPTION OF THE DRAWINGS

The accompanying colored photographs illustrate the overall appearance and distinct characteristics of the new grape cultivar. The photographs were taken of five-year-old plants of the new cultivar as grown outdoors in a field in Saint-Ubalde, Québec, Canada.

The photograph in FIG. 1 provides a side view of the plant habit of 'Juneaudor précoce' with fruit clusters.

Figure 1:
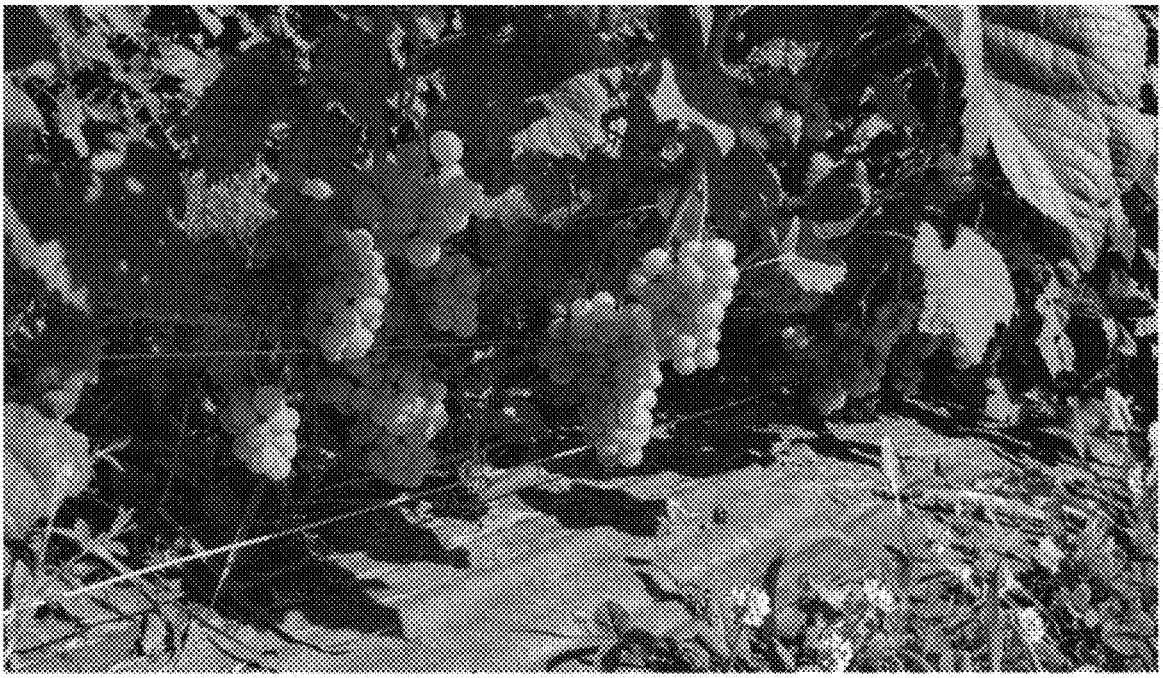
Figure 2:
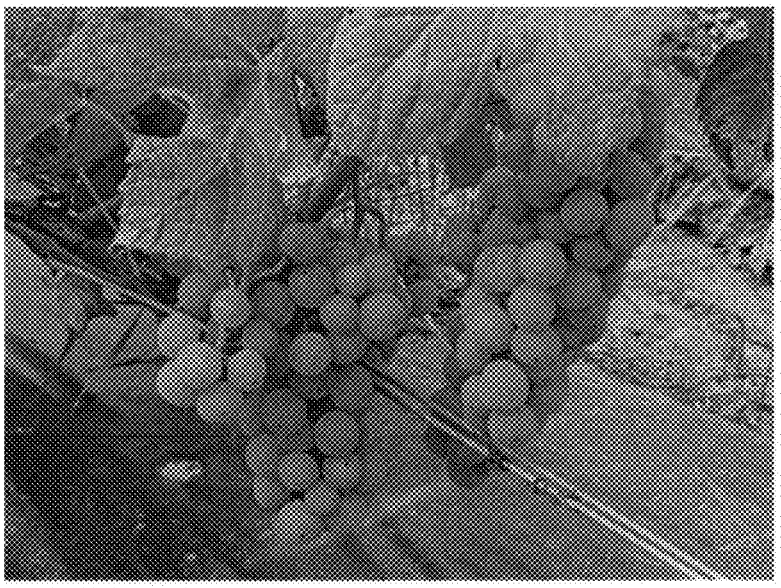

The photograph in FIG. 2 provides a close-up view of the immature fruit of 'Juneaudor précoce'.

Figure 3:
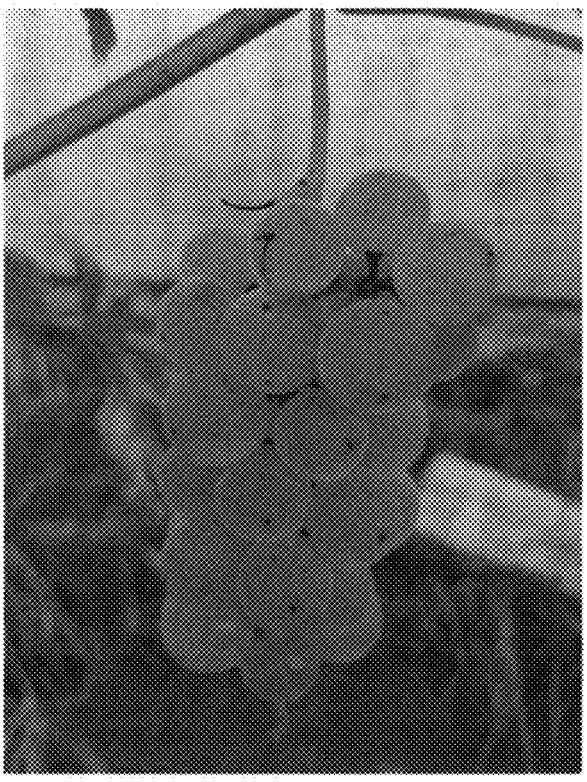

The photograph in FIG. 3 provides a close-up view of the mature fruit of 'Juneaudor précoce'.

Figure 4:
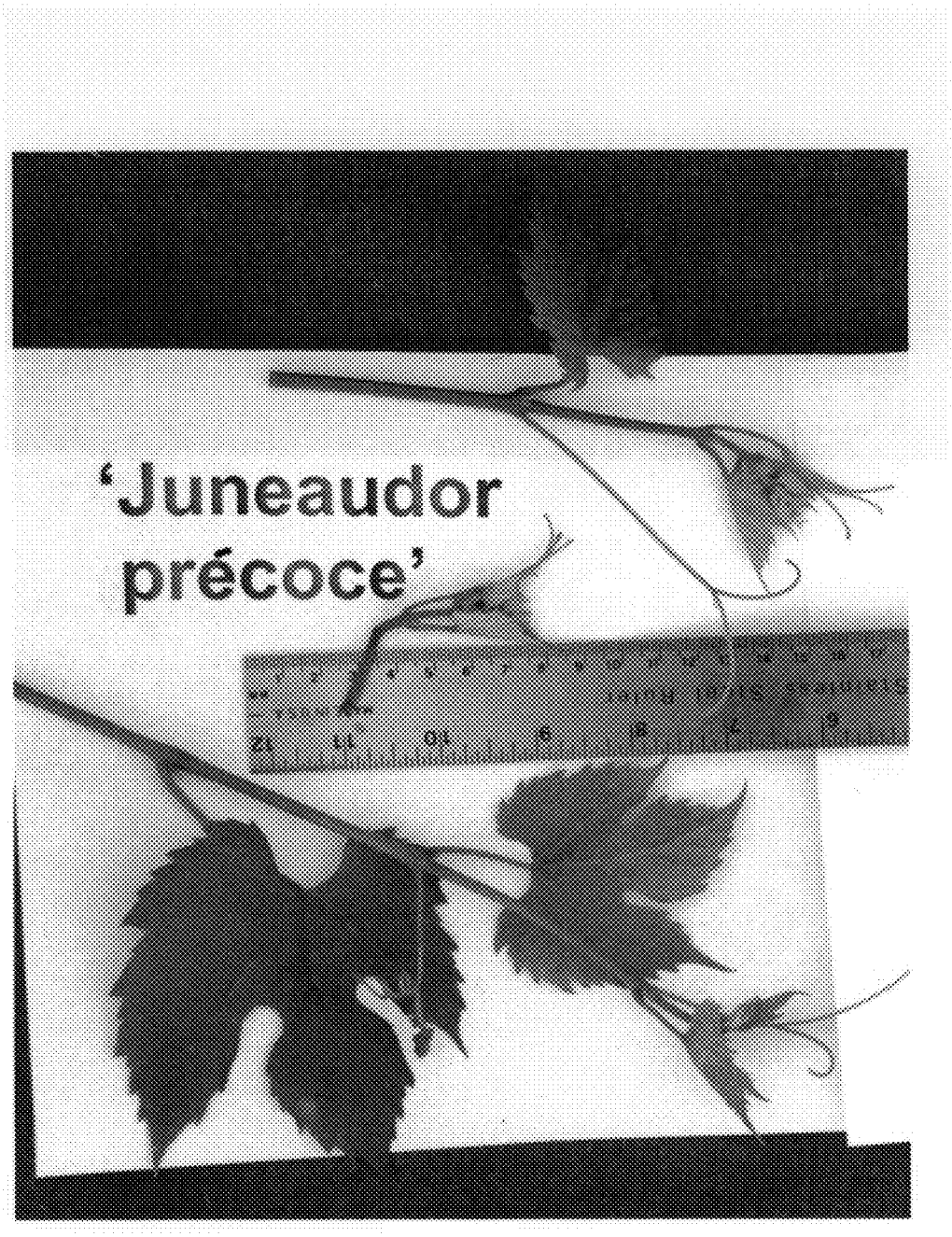

The photograph in FIG. 4 provides a view of the upper and lower leaf surfaces of 'Juneaudor précoce'.

The colors in the photographs are as close as possible with digital photography techniques available, the color values cited in the detailed botanical description accurately describe the colors of the new cultivar of grape.

DETAILED BOTANICAL DESCRIPTION OF THE PLANT

The following is a detailed description of plants five years in age as grown outdoors in a trial field in Saint-Ubalde, Québec, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Typically commences bloom on June 15$^{th}$ in the County of Portneuf, Québec.
*Plant type*.—Perennial fruit producing vine.
*Plant habit*.—Open and orderly.
*Height and spread*.—An average of 1.2 m in height and 220 cm in width.
*Cold hardiness*.—At least in U.S.D.A. Zone 4a.
*Propagation*.—Hardwood stem cuttings.
*Root description*.—Fibrous and fine.
*Root development*.—An average of 21 days for root initiation with a young plants produced from a rooted cutting produced in 45 to 60 days.
*Growth rate*.—Vigorous.

Mature canes:

*Color of canes*.—200B.
*Length of canes*.—Up to 1.40 m.
*Diameter of canes*.—10 mm.
*Diameter at nodes*.—12 mm.
*Internode length*.—10.5 cm.
*Lenticels*.—None.
*Cane cross-section shape*.—Round.
*Surface*.—Smooth with no hairs.
*Tendril pattern on shoot*.—2,0,2,0 etc. (two nodes with a tendril followed by one node without).
*Tendrils forked*.—Yes.
*Tendril texture*.—Glabrous.
*Tendril length*.—11 to 15 cm in length, 2 to 3 mm in width.
*Tendril color*.—Color on young shoots N144A, mature 144B.
*Bud width*.—2 mm.
*Bud length*.—5 mm.
*Bud shape*.—Triangular.
*Bud color*.—144B.
*Bud burst*.—Early.

Trunk:

*Bark texture*.—Roughly striated.
*Bark color*.—200C to 200D.
*Trunk shape*.—Oval-round.
*Trunk diameter*.—An average of 56 cm on diameter measured 20 cm above soil line for a five year-old-plant.

Mature leaves:

*Length of blade*.—11.9 cm.
*Width of blade*.—12.5 cm.
*Shape of blade*.—Pentagonal to wedge-shaped.
*Number of lobes*.—3.
*Blade margins*.—Incised into lobes with lobes serrated.
*Length of primary (midrib) vein n1 from the tip of the blade to the petiole sinus*.—9.1 cm.
*Length of petiole compared to length of middle vein (midrib)*.—Nearly equal.
*Length of vein n2 from the tip of the first major lobe of the blade to the petiole sinus*.—7.8 cm.
*Length of vein n3 from the tip of the second major lobe of the blade to the petiole sinus*.—5.8 cm.
*Length of vein n4 from the tip of the third major lobe of the blade to where it joins the vein measured in n3*.—3.0 cm.
*Length of vein n5 from the tip of the first tooth proximal to the petiole sinus to where it joins the vein measured in n4*.—0.8 cm.
*Leaf vein anthocyanin*.—None.
*Length of n2 teeth*.—0.65 cm.
*Width of n2 teeth*.—0.90 cm.
*Length to width ratio of n2 teeth*.—Small, <1:1.
*Length of n4 teeth*.—0.3 cm.
*Width of n4 teeth*.—0.2 cm.
*Length to width ratio of n4 teeth*.—Small, 1:1.
*Shape of teeth*.—Slightly convex on both sides.
*Arrangement of petiolar sinus*.—Wide open.
*Shape of base of petiolar sinus*.—Wide, v-shaped.
*Depth of petiolar sinus*.—2.5 cm.
*Width of petiolar sinus*.—3.2 cm.
*Petiole*.—9.3 cm in length, 2 to 3 mm in width.
*Shape of upper sinuses*.—Narrow v to u-shaped.
*Shape of base of upper sinuses*.—U-shaped.
*Arrangement of upper sinuses*.—Wide open.
*Glossiness of adaxial and abaxial surface*.—None.
*Pubescence on adaxial surface*.—None.
*Pubescence on abaxial surface*.—Very small erect hairs on veins, sparse prostrate hairs between veins.
*Blistering on adaxial surface*.—None.
*Color of adaxial leaf surface*.—144A, fall color not distinct.
*Color of abaxial leaf surface*.—144B to 144C, fall color not distinct.
*Color of leaf petiole*.—144A to 144B in color.
*Center lobe size*.—6.5 cm in length and 5.5 cm in width.
*Lateral lobe size*.—6 cm in length and 6.5 cm in width.
*Basal lobe size*.—NA.
*Density of foliage*.—Moderate.

Young shoots:

*Form of shoot tip*.—Half open.
*Density of prostate hairs on tip*.—Absent.
*Density of erect hairs on tip*.—Absent, a sparce amount of prostrate hairs are present between the veins on the abaxial or dorsal side of the young leaves (no anthocyanin coloration).
*Petiole pigmentation*.—A blend of N144B and N144C.

*Shoot attitude*.—Semi-erect before tying.

*Shoot pigmentation* (*internodes and nodes*).—A blend of 144B and 144C on the ventral side and on the dorsal side.

*Young leaves and first six distal unfolded leaves*.—A blend of N144C and 144B to 144C in color on the upper surface, and a blend of 144D to 192C and 192D on the lower surface with a faint anthocyanin blush of 186C and 186D along the margins and tips of the upper lobes, lower surface; very small erect hairs on veins, sparse prostrate hairs between veins.

Flower description:

*Fragrance*.—Slightly fragrant.

*Mean time of flowering*.—About June 15th in Portneuf County, Québec, Canada.

*Color of calyx*.—143B.

*Flowering shoot vigor*.—Vigorous.

*Flowering shoot attitude*.—Semi-erect without tying.

*Sepal number*.—5, sepals fused into continuous calyx.

*Calyx shape*.—Ring-shaped.

*Calyx size*.—Length; <1 mm in, width; 2 mm.

*Calyx apex*.—Fused to ovary.

*Calyx base*.—Fused to pedicel.

*Nectary*.—1.5 mm in diameter, <1 mm in length, 143C in colour.

*Calyx surface*.—Glabrous.

*Petals*.—5, fused in calyptra cohering at summit; 2.5 mm in width and 1 mm in depth and separating at base; 4 mm in width, 2 mm in depth; reflexed after dehiscence, 144A in color.

*Shape of cluster*.—Slightly conical, with shoulders.

*Number of flowers/cluster*.—Average of 100, 20 on wings.

*No of clusters per cane*.—Average of 4.

*Flower buds*.—4 mm in length, 2.5 mm in width, a blend between 144B and N144C in color, oblanceolate in shape, glabrous surface.

*Size of individual entire flower*.—4 mm in height, 1.5 cm in width (to end of stamens).

*Pollen fertility*.—Fertile based on use in controlled crosses.

*Reproductive organs* (*bisexual*).—Fully developed stamens and fully developed gynoecium.

*Color of stamen*.—Anther; 4D, Filament; 160C to 160D.

*Stamen number*.—Average of 5.

*Filament length*.—5 mm.

*Anther*.—1.5 mm in length.

*Pollen quantity and color*.—Abundant and 10C in color.

*Pistil*.—1, ovary is 1.5 mm in length and 1 mm in width at base, urn-shaped, glabrous surface, color 144A to 144B, stigma 1 mm in width and <1 mm in length, color 154C.

*Pedicel*.—3.5 mm and <1 mm in width, surface glabrous, color 144C.

*Peduncle*.—To base of cluster 4.5 cm and 3 to 4 mm in width (primary bunch), glossy surface and 144A in color and suffused with 184B, semi-lignified when fruit is ripe.

*Position of first first flowering and fruiting node*.—Typically node 2 but variable due to shoot pruning.

Fruit:

*Cluster* (*bunch*) *length*.—11.7 cm.

*Cluster* (*bunch*) *diameter*.—5.9 cm.

*Cluster weight*.—98 g.

*Cluster* (*bunch*) *density*.—Loose, average of 75 berries per cluster.

*Cluster no*.—An average of 2.5 per bud.

*Berry weight*.—2.2 g.

*Berry length*.—1.5 cm.

*Berry diameter at equator*.—1.7 cm.

*Berry shape*.—Round.

*Berry cross-section*.—Circular.

*Berry, color of skin*.—Golden; a blend of 153D and 154A to 154B, immature 144C.

*Berry, color of flesh*.—157A to 157B (no anthocyanin).

*Berry flesh firmness*.—Firm.

*Berry skin thickness*.—Thick.

*Berry skin bloom* (*cuticular wax*).—Minimal.

*Berry reticulation*.—None observed.

*Berry skin tenacity to skin*.—Moderate.

*Berry size uniformity*.—Very uniform.

*Berry, particular flavor*.—Sweet, not strongly aromatic.

*Length of pedicel*.—4 mm.

*Pedicel diameter*.—1.4 mm.

*Pedicel color*.—144B.

*Berry, separation from pedicel*.—Difficult.

*Berry, presence of seeds*.—Fully developed.

*Seed number per berry*.—2.

*Seed length*.—5 mm.

*Seed width*.—4 mm.

*Seed length to width ratio*.—Small, 1:1.

*Seed weight*.—0.03 g.

*Seed color*.—A blend of 199A to 199B.

Fruit: Values represent the means (with ranges in parentheses) for fruit harvested over five growing seasons 2016-2020.

*Harvest date*.—Average of August 30 (August 24 to September 15).

*Time of beginning berry ripening*.—Third week in August.

*Brix*.—18.6 (15 to 22).

*Ph*.—3.42 (3.1 to 3.42).

*Titratable acidity*.—8.2 to 11.92 (season 2020).

*Berry use*.—wine production.

*Berry storage*.—Not applicable, used directly for wine making when ripe.

Vineyard performance: Based on observations compiled over five years (2016-2020).

*Susceptibility to powdery mildew* (*uncinula necator*).—None, presumed resistant.

*Susceptibility to downy mildew* (*plasmopara viticola*).—None, presumed resistant.

*Susceptibility to black rot* (*guignardia bidwellii*).—None, presumed resistant.

*Susceptibility to grey mold* (*botrytis cinerea*).—Medium.

*Susceptibility to foliar phylloxera* (*daktulosphaira vitifoliae*).—None present.

*Susceptibility to crown gall* (*agrobacterium tumefaciens*).—Low.

*Susceptibility to phenoxy herbicide drift* (e.g., 2,4-D).—None present in Vineyard.

*Pests*.—No susceptibility or resistance has been observed.

*Berry splitting*.—None.

*Berry shelling*. None.

*Vigor level*.—High.
*Wood ripening*.—Good.
Wine quality:
*Flavors and aromas*.—Vinous with a fruity taste, rich aroma.
*Balance*.—Well balanced.
*Color*.—White.
*Propensity for oxidation*.—None.
*Overall quality*.—Very good.

It is claimed:

1. A new and distinct cultivar of Grape plant named 'Juneaudor précoce' as herein illustrated and described.

* * * * *